(12) United States Patent
Flaeschner et al.

(10) Patent No.: US 12,017,089 B2
(45) Date of Patent: Jun. 25, 2024

(54) PLANNING APPARATUS FOR PLANNING A RADIATION THERAPY

(71) Applicant: KONINKLIJKE PHILIPS N.V., Eindhoven (NL)

(72) Inventors: Nick Flaeschner, Hamburg (DE); Harald Sepp Heese, Hamburg (DE); Maria Luiza Bondar, Waalre (NL); Kay Sun, Fitchburg, MA (US); Jens Wiegert, Aachen (DE); Rolf Juergen Weese, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 365 days.

(21) Appl. No.: 17/558,637

(22) Filed: Dec. 22, 2021

(65) Prior Publication Data

US 2022/0203124 A1 Jun. 30, 2022

Related U.S. Application Data

(60) Provisional application No. 63/128,901, filed on Dec. 22, 2020.

(30) Foreign Application Priority Data

Jan. 25, 2021 (EP) .................................... 21153229

(51) Int. Cl.
*A61N 5/10* (2006.01)
(52) U.S. Cl.
CPC ......... *A61N 5/1039* (2013.01); *A61N 5/1045* (2013.01)

(58) Field of Classification Search
None
See application file for complete search history.

(56) References Cited

U.S. PATENT DOCUMENTS

| | | |
|---|---|---|
| 2013/0197878 A1 | 8/2013 | Fiege |
| 2019/0030370 A1 | 1/2019 | Hibbard |
| 2019/0108904 A1 | 4/2019 | Zhou |

(Continued)

FOREIGN PATENT DOCUMENTS

WO 2018048575 A1 3/2018

OTHER PUBLICATIONS

Lee, Hoyeon et al "Fluence-map generation for prostate intensity-modulated radiotherapy planning using a deep-neural-network", Scientific Reports Nature Research, 2019.

(Continued)

*Primary Examiner* — Marcus H Taningco
(74) *Attorney, Agent, or Firm* — Sherry Austin

(57) ABSTRACT

The invention relates to a planning apparatus for planning a radiation therapy. A medical image, in which a target to be irradiated is indicated, is reformatted based on ray geometries to be used during the radiation therapy to be planned, resulting in several reformatted medical images. Radiation therapy parameters being indicative of intensities of rays 5 to be used for irradiating a target 4 are determined based on the reformatted medical images by using a neural network unit. This allows to determine high quality radiation therapy parameters and hence allows for an improved planning of a radiation therapy. In particular, radiation and absorptions physics can be captured better, which can lead to the improved quality.

15 Claims, 13 Drawing Sheets

(56) References Cited

U.S. PATENT DOCUMENTS

2019/0175952 A1* 6/2019 Hissoiny .............. A61N 5/1049
2019/0362522 A1 11/2019 Han
2020/0075148 A1 3/2020 Nguyen
2022/0249868 A1* 8/2022 Fay ..................... G06F 21/6254
2023/0128148 A1* 4/2023 Li ....................... A61N 5/1036
600/1

OTHER PUBLICATIONS

Ogunmolu, Okalekan et al "Deep BOO! Automating Beam Orientation Optimization in Intensity-Modulated Radiation Therapy", 2019.

Fan, Jiawei et al, "Automatic treatment planning based on three-dimensional dose distribution predicted from deep learning technique", Medical Physics 2019, vol. 46 (1), pp. 370-381.

Nguyen, Dan et al, "A feasibility study for predicting optimal radiation therapy dose distributions of prostate cancer patients from patient anatomy using deep learning", Scientific Reports, 2019, 9, 1076.

Barragán-Montero, Ana Maria "Three-Dimensional Dose Prediction for Lung IMRT Patients with Deep Neural Networks: Robust Learning from Heterogeneous Beam Configurations", Medical Physics, vol. 46, No. 8, Aug. 2019.

Good, David et al A Knowledge-Based Approach to Improving and Homogenizing Intensity Modulated Radiation Therapy Planning Quality Among Treatment Centers: An Example Application to Prostate Cancer Planning; Int. J. Rad. Oncol. Biol. Phys. 2013, 87(1), 176-181—Abstract Only.

Brosch, Tom et al "Foveal fully convolutional nets for multi-organ segmentation", Proc. SPIE 10574, Medical Imaging 2018: Image Processing, Abstract Only.

* cited by examiner

PLANNING APPARATUS FOR PLANNING A RADIATION THERAPY

FIELD OF THE INVENTION

The invention relates to a planning apparatus, a planning method and a planning computer program for planning a radiation therapy. Moreover, the invention relates to a training apparatus, a training method and a training computer program for training a neural network unit, and to a radiation therapy system comprising the planning apparatus.

BACKGROUND OF THE INVENTION

WO 2018/048575 A1 discloses a planning apparatus for planning an intensity-modulated radiotherapy (IMRT). The planning includes determining a radiation dose distribution by using a neural network based on given clinical targets. However, the generated radiation dose distribution might not be physically feasible, i.e. the generated radiation dose distribution might fulfil all clinical targets, but it might not be realizable because of not having captured radiation and absorption physics well enough. This might lead to a reduced planning quality.

SUMMARY OF THE INVENTION

It is an object of the present invention to provide a planning apparatus, a planning method and a planning computer program which allow for an improved planning of a radiation therapy. It is a further object of the present invention to provide a training apparatus, a training method and a training computer program for training a neural network unit which could, after training, be used by the planning apparatus, the planning method and the planning computer program such that the planning can be improved. It is a further object of the present invention to provide a radiation therapy system comprising the planning apparatus.

In a first aspect of the present invention a planning apparatus for planning a radiation therapy is presented, wherein the planning apparatus comprises:
  a medical image provider configured to provide a medical image of a subject, wherein in the medical image a target to be treated with radiation beams is indicated,
  a ray geometry provider configured to provide ray geometries for different radiation beams to be used for irradiating the target, wherein a respective radiation beam comprises respective rays and a respective ray geometry defines, for the respective radiation beam, positions of the respective rays of the respective radiation beam,
  a reformatter configured to reformat the provided medical image based on the provided ray geometries, resulting in several reformatted medical images, wherein a respective reformatted medical image results from reformatting the provided medical image in accordance with a respective ray geometry,
  a neural network provider configured to provide a neural network unit which has been trained to output radiation therapy parameters being indicative of intensities of rays of radiation beams to be used during the radiation therapy based on an input which depends on reformatted medical images in which a target to be treated with radiation beams is indicated and which have been reformatted in accordance with ray geometries of the rays of the radiation beams,
  a radiation therapy parameters determiner configured to determine radiation therapy parameters being indicative of intensities of the rays of the radiation beams to be used for irradiating the target based on the reformatted medical images by using the provided neural network unit.

This allows to determine high quality radiation therapy parameters and hence allows for an improved planning of a radiation therapy. In particular, radiation and absorptions physics can be captured better, which can lead to the improved quality.

In the medical image also a risk structure can be indicated. In particular, in the medical image the target and the risk structure are preferentially indicated by indicating which image element, for instance, which voxel, of the medical image shows a part of the target and which image element shows a part of the risk structure. In particular, the image elements can be classified as being, for instance, a target image element or a risk structure image element. The provision of this information could also be regarded as being a masking, wherein the masking defines which image element belongs to the target and which image element belongs to the risk structure. A respective image element can therefore comprise at least two image values, i.e. an image display value and a mask value. The image display value indicates how the respective image element should be displayed. A respective image element can comprise a single image display value like an image intensity value, or several image display values like an image intensity value, an image color value and/or an image saturation value. Moreover, the mask value indicates whether the respective image element is, for instance, an image element of the target, of the risk structure or of another component of the subject shown in the medical image. Since to a respective image element at least an image display value and a mask value are assigned, this could also be regarded as assigning to the respective image element an image vector comprising the at least one image display value and the mask value. Thus, in a preferred embodiment to each image element of the medical image and to each image element of the reformatted medical images a respective vector is assigned, which comprises at least one image display value like an image intensity and a mask value.

In an embodiment, the mask values might not only indicate the respective classification, i.e., for instance, whether the respective image element belongs to the target, the risk structure or neither to the target nor the risk structure, but they might also indicate dose related values. For example, for image elements, which belong to a target, target doses can be indicated. For image elements, which belong to a risk structure, maximum radiation doses can be indicated. In an embodiment, the mask values indicate which image elements belong to the target and, for these image elements and hence for these parts of the target, target doses are indicated, and they indicate which image elements belong to the risk structure. In particular, for the target a set of target mask values might be provided, wherein these target mask values indicate which image elements belong to the target and which image elements do not belong to the target, wherein these target mask values might further indicate, for the image elements belonging to the target, a respective dose related value like a respective target dose. For the risk structure a set of risk structure mask values might be provided, wherein these risk structure mask values indicate which image elements belong to the risk structure and which image elements do not belong to the risk structure, wherein these risk structure mask values might further indicate, for the image elements belonging to the risk structure, a respective dose related value like a respective maximum dose. Thus, in an embodiment, to each image element of the medical image and to each image element of the reformatted medical images a respective vector can be assigned, which comprises at least one image display value like an image intensity and at least one mask value, wherein the at least mask value might include a target mask value and optionally also a risk structure mask value if a risk structure should be considered.

The medical image indicating the target and optionally also a risk structure is therefore preferentially a data set in which to each image element at least one image display value and at least one mask value is assigned, wherein the latter at least indicates whether the respective image element belongs to the target or not.

The target is, for instance, a tumor and the risk structure is, for example, an organ which should not be adversely affected by the radiation beams. In the medical image a single risk structure or several risk structures can be indicated. The medical image provider is preferentially configured to provide a computed tomography (CT) image as the medical image.

The reformatter is preferentially configured to interpolate the image values and mask values such that they are located along the rays defined by the ray geometry. For instance, for interpolating the image values a linear interpolation or spline interpolation might be used. If the mask values just indicate whether the respective image elements belong to a target, a risk structure or neither to a target nor to a risk structure, the interpolation is preferentially a nearest neighbor interpolation, wherein in this case the mask values might be integer values. If the mask values comprise dose related values, also a linear interpolation or a spline interpolation might be used.

The medical image provider can be a storage unit which is configured to store the medial image and to provide the stored medical image. The medical image provider can also be a receiver for receiving the medical image from another device like a medical imaging system and for providing the received medical image. The medical image provider can also be the medical imaging system itself. The medical image received by the medical image provider might already comprise indications for indicating the target to be treated with radiation beams and optionally one or several risk structures. However, it is also possible that the medical image provider itself automatically provides this indication by, for instance, segmenting the target and optionally one or several risk structures in the medical image. The medical image provider could also comprise a graphical user interface for allowing a user to indicate the target and optionally one or several risk structures within the medical image and/or in order to modify a given indication of the target and optionally one or several risk structures within the medical image.

The ray geometry provider can also be a storage unit in which the ray geometries are stored and from which the stored ray geometries can be provided. The ray geometry provider can also be a receiver for receiving ray geometries and for providing the received ray geometries. Moreover, the ray geometry provider can also be configured to determine the ray geometries and to provide the determined ray geometries. For instance, the ray geometry provider can be adapted to determine the ray geometries based on a given delivery protocol defining, for example, in which beam directions the target should be irradiated.

The neural network provider can also be a storage unit which in this case is configured to store the neural network unit and to provide the stored neural network unit. However, it is also possible that the neural network provider is a receiver for receiving the neural network unit and for providing the received neural network unit. The neural network provider can also be a trainer configured to train an initial neural network unit or an already trained neural network unit and to provide the trained neural network unit.

In an embodiment the ray geometry provider is configured to define for a respective radiation beam a respective virtual planar region between a radiation source configured to generate the radiation beams and the subject, wherein the respective virtual planar region is subdivided into bixels and wherein a respective ray geometry defines that a respective ray traverses a respective bixel. Preferentially, a respective ray traverses the center of a respective bixel. The virtual planar region can be regarded as being a virtual planar region of a fluence map and hence as a fluence plane, wherein the determined radiation therapy parameters can indicate the fluence at each bixel of the fluence map, in order to indicate the intensities of the rays of the radiation beams to be used for irradiating the target. This allows to determine fluence maps which define physically feasible dose distributions, wherein it might only be required to adapt the fluence maps to machine constraints of a radiation therapy system like a LINAC ("linear accelerator").

Preferentially, the radiation beams to be used for irradiating the target are generated by using a radiation source for providing radiation and a multileaf collimator configured to provide different leaf openings for shaping the generated radiation, wherein the radiation source and the multileaf collimator are rotatable around the subject, in order to allow to provide the radiation beams in different radiation directions. The radiation therapy parameters can indicate intensities of the radiation generated by the radiation source and leaf openings of the multileaf collimator for the radiation beams, in order to indicate the intensities of the rays of the radiation beams. In particular, the radiation therapy parameters can directly indicate how the radiation source and the multileaf collimator should be controlled, thereby allowing for a very fast transformation of the planned radiation therapy into control parameters for controlling the radiation source and the multileaf collimator.

It is preferred that the neural network unit comprises a first part with a first convolutional network and a second part with a second convolutional network, wherein the first part receives the reformatted medical images as input and provides its output to the second part, wherein the second part receives the output of the first part and outputs the radiation therapy parameters. Preferentially, the first convolutional network comprises a sequence of convolutional layers, wherein each convolutional layer comprises one or several filters, wherein the first convolutional layer of this sequence receives the reformatted medical images which might be preprocessed before being received by the first convolutional layer. In particular, the number of the filters of the last convolutional layer of the sequence is smaller than the number of elements of a respective reformatted medical image in a direction of a respective ray. In this way, the number of elements output by the last convolutional layer and hence the amount of data to be further processed by the neural network unit can be decreased, which allows for a further reduction of computational efforts. It has been found that information of the reformatted medical images in ray direction can be significantly condensed, without reducing the quality of the finally determined radiation therapy parameters. Thus, the computational efforts can be reduced, without diminishing the quality of the finally determined radiation therapy parameters.

The reformatted medical images received by the first convolutional layer can be preprocessed before being received. Thus, the reformatted medical images received by the first convolutional layer can be preprocessed or not.

Preferentially, the first convolutional network is a multi-resolution convolutional network. In particular, the first part of the neural network unit, which comprises the first convolutional network, is configured to, for a respective reformatted medical image, i) determine several intermediate reformatted medical images having different resolutions by modifying the resolution of the respective reformatted medical image, ii) provide the intermediate reformatted medical images as input to the first convolutional network such that for a respective intermediate reformatted medical image a respective first intermediate feature set is output by the first convolutional network, thereby producing several first intermediate feature sets having different resolutions, and iii) combine the several first intermediate feature sets having different resolutions such that a feature set is obtained for a respective reformatted medical image, which is to be input into the second part of the neural network, wherein the combining includes, starting from a first intermediate feature set having the smallest resolution, a) modifying the first intermediate feature set such that its resolution is similar to the next larger one of the resolutions of the several first intermediate feature sets, b) concatenating the modified first intermediate feature set having the modified resolution with the first intermediate feature set having the same resolution, thereby generating a combined feature set, c) modifying the combined feature set such that its resolution is similar to the next larger one of the resolutions of the several first intermediate feature sets, and d) concatenating the modified combined feature set having the modified resolution with the first intermediate feature set having the same resolution, thereby generating a further combined feature set, wherein steps c) and d) are repeated, until a final combined feature set is obtained, which is the feature set to be input into the second part of the neural network unit. By using different resolutions, information in the medical image in different degrees of detail can be very effectively considered. In particular, a reduced resolution for a "larger context" reduces the number of parameters such that less training data are needed and the computational burden can be reduced.

Preferentially, the first part also includes a batch normalization and/or an activation function. The activation function is preferentially a rectified linear activation function which might also be named "ReLU". The batch normalization and the activation function can improve the training of the neural network, i.e. the learning of the determination of the radiation therapy parameters, and hence finally lead to a more accurate determination. In particular, the activation function can add a non-linearity to the neural network, wherein the ReLU can further improve the learning in comparison to less suited activation functions.

It is further preferred that the first part of the neural network unit is configured to output for a respective reformatted medical image a respective feature set, wherein the second part of the neural network unit is configured to concatenate the feature sets output by the first part in accordance with a concatenation rule in a concatenation direction, thereby generating a concatenated feature set, and to provide the concatenated feature set as input to the second convolutional network. In an embodiment the feature sets to be concatenated each comprise a first direction and a second direction corresponding to directions spanning the virtual planar region, which might be regarded as defining a fluence plane, and a third direction perpendicular to the first direction and the second direction, wherein the concatenation rule defines that the concatenation direction is one of the first direction, the second direction and the third direction.

In an embodiment, the concatenation rule defines that the feature sets are concatenated in the concatenation direction such that in this direction the sets of features are grouped with respect to the beam direction of the respective radiation beam. In a further embodiment, the concatenation rule defines that, before concatenating the several feature sets, a respective feature set is subdivided into respective feature subsets and that the several feature subsets are concatenated such that feature subsets corresponding to different feature sets are adjacent to each other. By concatenating in this way, data, which are related to each other via, for instance, physics, are also close to each other in the data representation to which the neural network is applied. This leads to meaningful patterns which can very well be learned, thereby improving the training and hence also finally the use of the neural network unit.

In an embodiment, the concatenation rule defines that the feature sets output by the first part are concatenated based on directions of the radiation beams comprising the rays with the ray geometry according to which the respective reformation has been carried out. For instance, the concatenation can be carried out such that sets of features, which correspond to opposing beam directions, are adjacent to each other in the concatenated set of features. This reflects the fact that counter-propagating beam pairs can have a strong influence on the respective fluence map, wherein this can lead to a learning of more meaningful weights and hence to a further improved learning.

Preferentially, the second convolutional neural network is a fully convolutional neural network and/or a multi-resolution convolutional neural network. It is hence especially a multi-resolution fully convolutional neural network.

In an embodiment, the second part of the neural network unit is configured to, for a respective feature set to be input into the second convolutional network, i) determine several second intermediate feature sets having different resolutions by modifying the resolution of the respective feature set, ii) provide the second intermediate feature sets as input to the second convolutional network such that for a respective second intermediate feature set a respective third intermediate feature set is output, thereby producing several third intermediate feature sets having different resolutions, and iii) combine the several third intermediate feature sets having different resolutions such that a second combined feature set is obtained for a respective feature set, which is the output of the neural network unit, wherein the combining includes, starting from a third intermediate feature set having the smallest resolution, a) modifying the third intermediate feature set such that its resolution is similar to the next larger one of the resolutions of the several third intermediate feature sets, b) concatenating the modified third intermediate feature set having the modified resolution with the third intermediate feature set having the same resolution, thereby generating a combined feature set, c) modifying the combined feature set such that its resolution is similar to the next larger one of the resolutions of the several third intermediate feature sets, and d) concatenating the modified combined feature set having the modified resolution with the third intermediate feature set having the same resolution, thereby generating a third combined feature set, wherein steps c) and d) are repeated, until a final combined feature set is obtained, which is the output of the neural network unit. The output can be, for a respective beam direction, a respective fluence map, which is indicative of the intensity of the rays of the respective radiation beam. Thus, several fluence maps with different resolutions can be generated, which can be combined to the final fluence map.

In an embodiment, the second convolutional network comprises a network parameter that depends on the concatenation rule. For instance, the concatenation rule can define that the feature sets output by the first part are concatenated in a certain concatenation direction for generating the concatenated feature set, wherein the second convolutional neural network can comprise a network parameter that depends on the concatenation direction. The network parameter is, for instance, the size of a filter used by a convolutional layer of the second convolutional neural network. The network parameter can also be, for instance, the stride. In particular, the second convolutional neural network comprises a size of a filter and a stride as network parameters, wherein the size of the filter and the stride are determined such that along the concatenation direction the filter acts only on features of a same beam direction or several, but not all, beam directions at a same time. Thus, the size of the filter and the stride can be adapted to the geometry of the reformatted and concatenated image geometry, which can improve the learning of meaningful patterns by the filters.

In a further aspect of the present invention a training apparatus for training a neural network unit is presented, wherein the training apparatus comprises:
- a neural network provider configured provide a neural network unit to be trained,
- a training data sets provider configured to provide training data sets for training the provided neural network unit, wherein a training data set comprises as input training data a) a reformatted medical image, which is a medical image of a subject, in which a target to be treated with radiation beams and optionally one or several risk structures are indicated and which has been reformatted in accordance with a ray geometry of a radiation beam to be used for irradiating the target, wherein the radiation beam comprises rays and the ray geometry defines positions of the rays of the radiation beam, and as output training data b) radiation therapy parameters being indicative of intensities of the rays of the radiation beam to be used for irradiating the target,
- a trainer configured to modify the provided neural network unit such that a deviation measure being indicative of a deviation between a) obtained output data, which are obtained if the input training data of the training data sets are input into the neural network unit, and b) the output training data of the training data sets is reduced.

The neural network provider of the training apparatus can be a storage unit configured to store the neural network unit and to provide the stored neural network unit. The neural network provider can also be a receiver for receiving the neural network unit and for providing the received neural network unit. Moreover, the training data sets provider can be a storage unit configured to store training data sets and to provide the stored training data sets. The training data sets provider can also be a receiving unit for receiving training data sets and for providing the received training data sets.

In an embodiment, the training data sets provider is configured to also provide, for a training data set, a training dose distribution across the target and optionally across one or several risk structures, wherein the trainer is configured to determine a dose distribution across the target and optionally across one or several risk structures, which would be obtained if a radiation therapy in accordance with the obtained output data were carried out, and wherein the deviation measure is also indicative of a deviation between a) the determined dose distribution and b) the training dose distribution.

In another aspect of the present invention a radiation therapy system is presented, wherein the radiation therapy system comprises:
- a radiation source configured to generate radiation to be directed to a target of a subject to be treated,
- a multileaf collimator configured to collimate the generated radiation with different leaf openings, in order form different radiation beams,
- a mover configured to move the radiation source and the multileaf collimator relative to the subject such that the target is irradiatable by the different radiation beams in different irradiation directions,
- a planning apparatus for planning a radiation therapy as defined by any of claims 1 to 8, wherein the planning apparatus is configured to determine radiation therapy parameters being indicative of intensities of rays of the radiation beams to be used for irradiating the target,
- a controller configured to control the radiation source, the multileaf collimator and the mover depending on the determined radiation therapy parameters.

In a further aspect of the present invention a planning method for planning a radiation therapy is presented, wherein the planning method comprises:
- providing a medical image of a subject by a medical image provider, wherein in the medical image a target to be treated with radiation beams is indicated,
- providing ray geometries for different radiation beams to be used for irradiating the target by a ray geometry provider, wherein a respective radiation beam comprises respective rays and a respective ray geometry defines, for the respective radiation beam, positions of the respective rays of the respective radiation beam,
- reformatting the provided medical image based on the provided ray geometries by a reformatter, resulting in several reformatted medical images, wherein a respective reformatted medical image results from reformatting the provided medical image in accordance with a respective ray geometry,
- providing a neural network unit by a neural network provider, wherein the neural network unit has been trained to output radiation therapy parameters being indicative of intensities of rays of radiation beams to be used during the radiation therapy based on an input which depends on reformatted medical images in which a target to be treated with radiation beams is indicated and which have been reformatted in accordance with ray geometries of the rays of the radiation beams,
- determining radiation therapy parameters by a radiation therapy parameters determiner based on the reformatted medical images by using the provided neural network unit, wherein the radiation therapy parameters are indicative of intensities of the rays of the radiation beams to be used for irradiating the target.

In another aspect of the present invention a training method for training a neural network unit is presented, wherein the training method comprises:
- providing a neural network unit, which should be trained, by a neural network provider,
- providing training data sets for training the provided neural network unit by a training data sets provider, wherein a training data set comprises as input training data a) a reformatted medical image, which is a medical image of a subject, in which a target to be treated with radiation beams is indicated and which has been reformatted in accordance with a ray geometry of a radiation beam to be used for irradiating the target, wherein the radiation beam comprises rays and the ray geometry defines positions of the rays of the radiation beam, and as output training data b) radiation therapy parameters being indicative of intensities of the rays of the radiation beam to be used for irradiating the target, modifying the provided neural network unit such that a deviation measure being indicative of a deviation between a) obtained output data, which are obtained if the input training data of the training data sets are input into the neural network unit, and b) the output training data of the training data sets is reduced, by a trainer.

In a further aspect of the present invention a planning computer program for planning a radiation therapy is presented, wherein the computer program comprises program code means for causing a planning apparatus as defined by any of claims 1 to 8 to carry out the steps of the planning method as defined by claim 12, when the computer program is run on a computer controlling the planning apparatus.

In another aspect of the present invention a training computer program for training a neural network unit is presented, wherein the computer program comprises program code means for causing a training apparatus as defined by any of claims 9 and 10 to carry out the steps of the training method as defined by claim 13, when the computer program is run on a computer controlling the training apparatus.

It shall be understood that the planning apparatus of claim 1, the training apparatus of claim 9, the radiation therapy system of claim 11, the planning method of claim 12, the training method of claim 13, the planning computer program of claim 14, and the training computer program of claim 15, have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
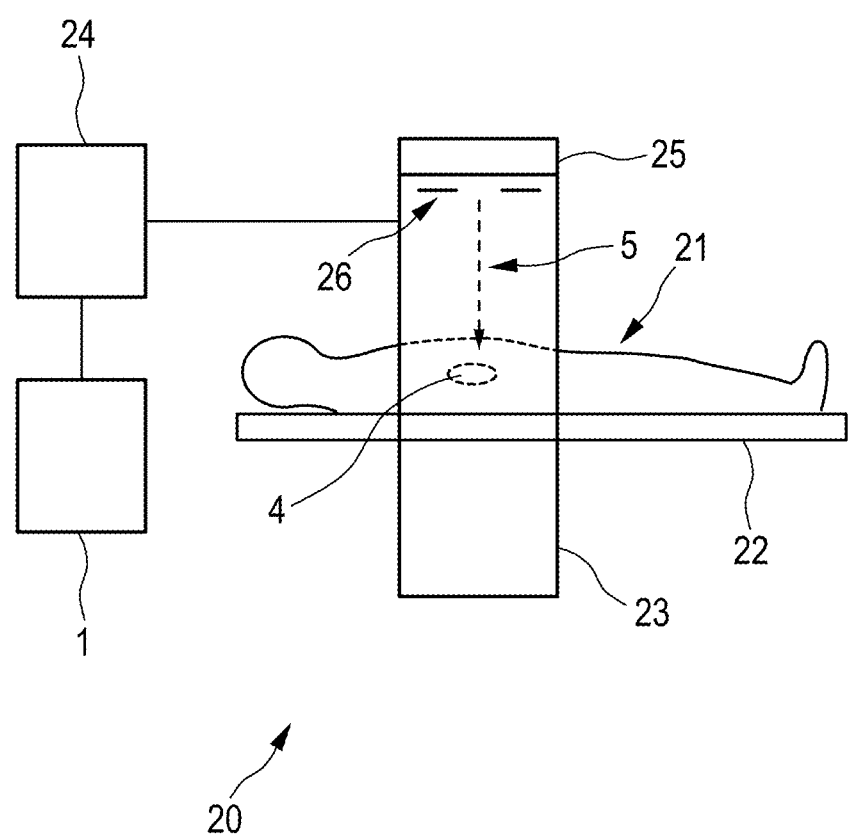
FIG. 1 shows schematically and exemplarily an embodiment of a radiation therapy system.

FIG. 1 shows schematically and exemplarily an embodiment of a radiation therapy system. The radiation therapy system 20 comprises a radiation source 25 configured to generate radiation to be directed to a target 4 within a subject 21 that is located on a support 22 like a patient table. The radiation therapy system 25 also comprises a multileaf collimator 26 configured to collimate the radiation generated by the radiation source 25 with different leaf openings, in order to form different radiation beams having different shapes. The multileaf collimator 26 is also schematically and exemplarily illustrated in FIG. 2.

The radiation therapy system 20 further comprises a mover configured to move the radiation source 25 and the multileaf collimator 26 relative to the subject 21 such that the target 4 is irradiatable by the different radiation beams in different irradiation directions. The mover 23 is preferentially a gantry to which the radiation source 25 and the multileaf collimator 26 are attached and which is rotatable around the support 22 and hence around the subject 21.

The radiation therapy system 20 further comprises a planning apparatus 1 for planning a radiation therapy, wherein the planning apparatus 1 is configured to determine radiation therapy parameters being indicative of intensities of rays of the radiation beams 5 to be used for irradiating the target 4. It should be noted that in this embodiment radiation therapy parameters being indicative of intensities of rays of radiation beams 5 indicate the intensity of the radiation generated by the radiation source 25 and the shape of the respective radiation beam as defined by the leaf opening of the multileaf collimator 26. The radiation therapy parameters being indicative of intensities of the rays of the radiation beams also indicate the position of the respective radiation beam. For instance, in an embodiment the radiation therapy parameters indicate, for different beam directions, intensities of the radiation generated by the radiation source 25 and leaf openings 28 of the multileaf collimator 26 for the radiation beams 5, in order to indicate the intensities of the rays of the radiation beams 5. It is also possible that the radiation therapy parameters indicate fluences 27 at bixels and hence a fluence map for different directions of the radiation beam, in order to indicate the intensities of the rays of the radiation beams 5 to be used for irradiating the target 4. The fluence map is preferentially provided in a respective virtual planar region 13 between the radiation source 25 and the subject 21, wherein the respective virtual planar region 13 is subdivided into bixels. The virtual planar region 13 can hence be regarded as being a virtual planar region of a fluence map or as a fluence plane, wherein the determined radiation therapy parameters can indicate the fluence at each bixel of the fluence map, in order to indicate the intensities of the rays of radiation beams 5 to be used for irradiating the target 4 as mentioned above.

Figure 3:
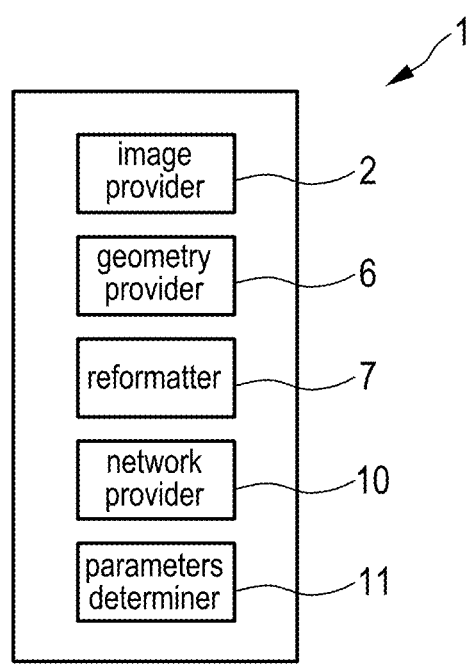
FIG. 3 shows schematically and exemplarily an embodiment of a planning apparatus for planning a radiation therapy.

The radiation therapy system 20 further comprises a controller 24 configured to control the radiation source 25, the multileaf collimator 26 and the mover 23, i.e., the gantry, depending on the radiation therapy parameters determined by the planning apparatus 1. The planning apparatus 1 will be explained in more detail in the following with reference to FIG. 3.

The planning apparatus 1 comprises a medical image provider 2 configured to provide a medical image 3 of the subject 21, wherein in the medical image 3 at least the target 4 to be treated with radiation beams 5 is indicated. In this embodiment, in the medical image 3 also a risk structure is indicated. In particular, in the medical image 3 the target 4 and the risk structure are indicated by indicating which image element, i.e., in this embodiment, which voxel, of the medical image 3 shows a part of the target 4 and which image element shows a part of the risk structure. The image elements can therefore be classified as being a target image element, a risk structure image element or neither a target image element nor a risk structure image element. This information can also be regarded as being masking information, wherein a corresponding mask value indicates whether the respective image element is a target image element, a risk structure element or neither a target image element nor a risk structure element. A respective image element can hence comprise at least two image values, i.e., an image display value and a mask value, wherein the image display value indicates how the respective image element should be displayed. In this embodiment, the image display value indicates an image intensity value like a grey value. Since, to a respective image element, a respective image display value and a respective mask value are assigned, i.e., since to each image element two values are assigned, this could be regarded as having to each image element assigned an image vector, wherein the respective image vector includes the image display value and the mask value.

The target 4 is, for instance, a tumor and the risk structure can be an organ or another part of the subject, which should not be adversely affected by the radiation beams 5. The medical image 3 can of course show no risk structure, a single risk structure or several risk structures. Moreover, the medical image is preferentially an anatomical image like a CT image or a magnetic resonance (MR) image.

The planning apparatus further comprises a ray geometry provider 6 configured to provide ray geometries for different radiation beams 5 to be used for irradiating the target 4, wherein a respective radiation beam 5 comprises respective rays and a respective ray geometry defines, for the respective radiation beam 5, positions of the respective rays of the respective radiation beam 5. In this embodiment, the respective ray geometry of a respective radiation beam 5 is defined such that a respective ray traverses a center of a respective bixel of a respective virtual planar region 13 for which a fluence map is to be determined.

Figure 4:
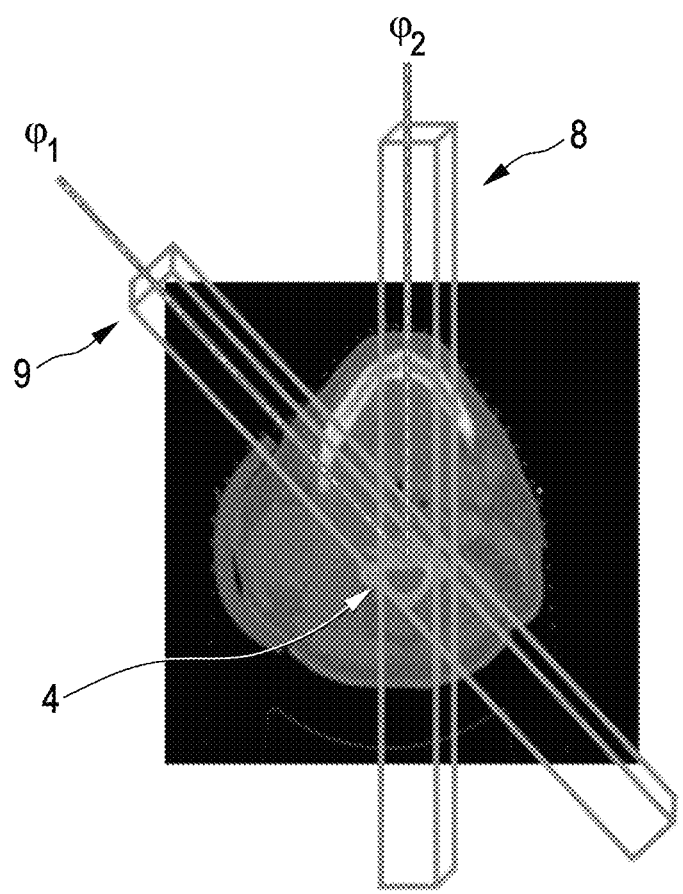
FIG. 4 illustrates schematically and exemplarily two reformatted medical images.

The planning apparatus further comprises a reformatter 7 configured to reformat the provided medical image 3 based on the provided ray geometries, of which two reformatted medical images 8, 9 are schematically and exemplarily illustrated in FIG. 4 for two different angular positions $\varphi_1$, $\varphi_2$ of the radiation source 25. A respective reformatted medical image 8, 9 results from reformatting the provided medical image 3 in accordance with a respective ray geometry. Although in FIG. 4 the respective reformatted medical image 8, 9 is illustrated as covering also parts outside of the initially provided medical image 3, in a preferred embodiment the respective reformatted medical image 8, 9 covers only a respective part of the initially provided medical image. For instance, the length of the respective reformatted medical image 8, 9 in the respective beam direction can be defined by the borders of the initially provided medical image or, for instance, by the borders of the subject shown in the initially provided medical image.

The reformatter 7 is preferentially configured to interpolate the image values and mask values such that they are located along the rays defined by the ray geometry. For instance, for interpolating the image values a linear interpolation or spline interpolation might be used. If the mask values just indicate whether the respective image elements belong to a target, a risk structure or neither to a target nor to a risk structure, the interpolation is preferentially a nearest neighbor interpolation, wherein in this case the mask values might be integer values. If the mask values comprise dose related values, also a linear interpolation or a spline interpolation might be used.

The planning apparatus further comprises a neural network provider 10 configured to provide a neural network unit 90 which has been trained to output radiation therapy parameters being indicative of intensities of rays of radiation beams to be used during the radiation therapy based on an input which depends on reformatted medical images in which a target to be treated with radiation beams and optionally a risk structure are indicated and which have been reformatted in accordance with ray geometries of the rays of the radiation beams. Moreover, the planning apparatus comprises a radiation therapy parameters determiner 11 configured to determine the radiation therapy parameters being indicative of intensities of the rays of the radiation beams 5 to be used for irradiating the target 4 and defining, in this embodiment, fluence maps based on the reformatted medical images 8, 9 by using the provided neural network unit 90.

Figure 5:
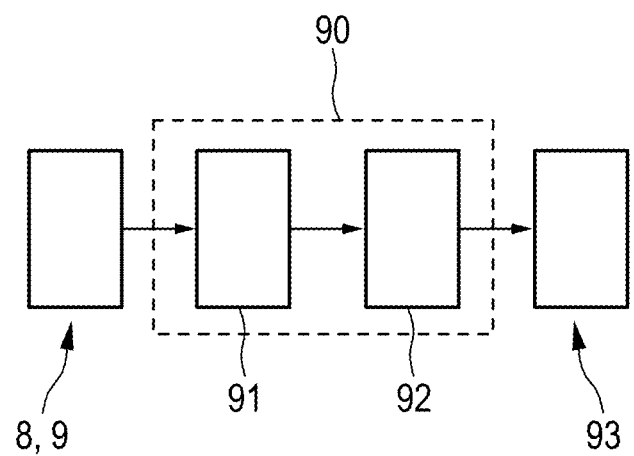
FIG. 5 shows schematically and exemplarily a neural network unit to be used by the planning apparatus for planning the radiation therapy.

The neural network unit 90 is schematically and exemplarily illustrated in FIG. 5. As can be seen in this figure, the neural network unit 90 comprises a first part 91 and a second part 92, wherein the first part 91 receives the reformatted medical images 8, 9 as input and provides its output to the second part 92. The second part 92 receives the output of the first part 91 and outputs the radiation therapy parameters 93 being, in this embodiment, fluence maps. The first part 91 comprises a first convolutional neural network with a sequence of convolutional layers, wherein each convolutional layer comprises one or several filters and wherein the first convolutional layer of the sequence receives the reformatted medical images 8, 9. The number of filters of the last convolutional layer of the sequence is smaller than the number of elements of a respective reformatted medical image 8, 9 in a direction of a respective ray. In this way, the number of elements output by the last convolutional layer of the first part 91 and hence the amount of data to be further processed by the second part 92 can be decreased, which allows for a reduction of computational efforts. Moreover, this forces the neural network unit to focus on the information which is really relevant for the present task.

The reformatted medical images 8, 9 received by the first convolutional layer of the first part 91 can be pre-processed before being received by the first convolutional layer. In particular, the first convolutional neural network of the part 91 of the neural network unit 90 is a multi-resolution convolutional neural network, wherein the reformatted medical images 8, 9 are modified such that different sets of reformatted medical images having different resolutions are provided, which are input to the first convolutional layer of the first convolutional neural network of the first part 91.

Thus, the first part 91 can be configured to, for a respective reformatted medical image 8, determine several intermediate reformatted medical images 70 having different resolutions by modifying the resolution of the respective reformatted medical image 8. The determined several intermediate reformatted medical images 70 having different resolutions are schematically and exemplarily illustrated in FIG. 6, wherein in FIG. 6 the intermediate reformatted medical image having a lower resolution is shown with a smaller size, because due to the lower resolution the number of elements of the respective intermediate reformatted medical image is smaller.

Figure 6:
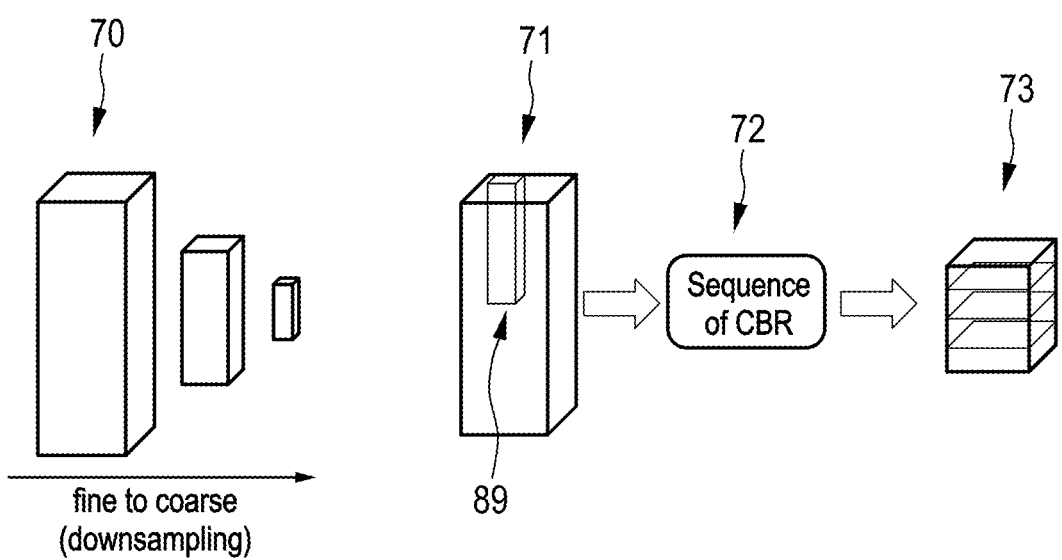
FIG. 6 illustrates schematically and exemplarily a determination of feature sets with different resolutions by using a first part of the neural network unit.
Figure 7:
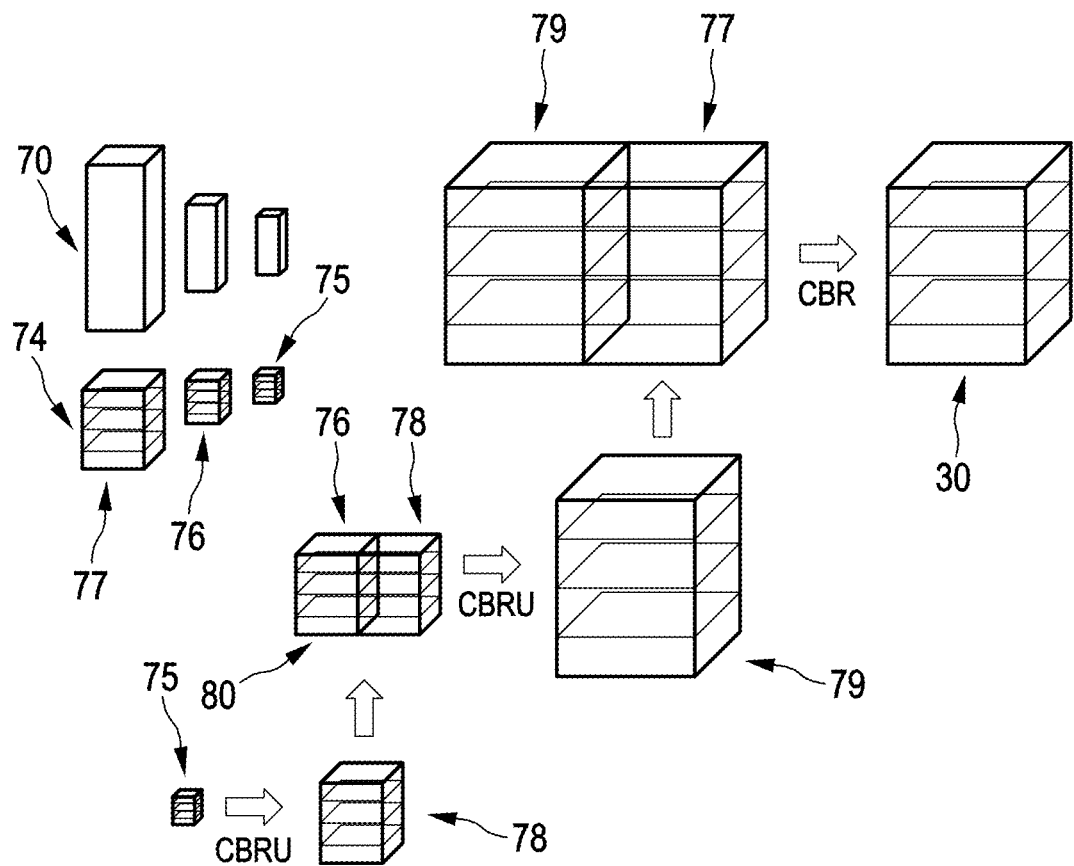
FIG. 7 illustrates schematically and exemplarily a concatenation of feature sets having different resolutions.

The intermediate reformatted medical images 70 are provided as input to the first convolutional neural network 72 of the first part 91 of the neural network 90 such that for a respective intermediate reformatted medical image 71 of the intermediate reformatted medical images 70 a respective first intermediate feature set 73 is output by the first convolutional neural network 72 as schematically and exemplarily illustrated in the right part of FIG. 6. This leads to a set 74 of several first intermediate feature sets having different resolutions which are schematically and exemplarily illustrated in FIG. 7. The first part 91 of the neural network unit 90 preferentially also includes a batch normalization and an activation function, particularly a rectified linear activation function. It is hereby noted that in FIG. 6 the box 89 indicates a convolutional kernel of the first convolutional network 72 which strides across the volume.

The first part 91 of the neural network unit 90 combines the several first intermediate feature sets 74 having different resolutions such that a feature set 30 is obtained for a respective reformatted medical image 8, wherein the respective feature set 30 is to be input into the second part 92 of the neural network. The combining includes, starting from a first intermediate feature set 75 having the smallest resolution, a) modifying the first intermediate feature set 75 such that its resolution is similar to the next larger one 76 of the resolutions of the several first intermediate feature sets 74, b) concatenating the modified first intermediate feature set 78 having the modified resolution with the first intermediate feature set 76 having the same resolution, thereby generating a combined feature set 80, c) modifying the combined feature set 80 such that its resolution is similar to the next larger one 77 of the resolutions of the several first intermediate feature set 74, and d) concatenating the modified combined feature set 79 having the modified resolution with the first intermediate feature set 77 having the same resolution, thereby generating a further combined feature set 30, wherein steps c) and d) are repeated, until a final combined feature set 30 is obtained, which is the feature set 30 to be input into the second part 92 of the neural network unit 90.

For generating a respective combined feature set by concatenating, i.e. for the respective aggregation, a convolutional neural network optionally with batch normalization and/or an activation function such as ReLU might be used. For the modification of the resolution of the respective feature set also a convolutional neural network optionally with batch normalization and/or an activation function such as ReLU might be used. However, for instance, the increasing of the resolution might also be an upsampling step, without using a neural network.

The first part 91 of the neural network 90 is hence configured to output for a respective reformatted medical image 8 a respective feature set 30, wherein the second part 92 of the neural network 90 is configured to concatenate the feature sets output by the first part 91 in accordance with a concatenation rule, thereby generating a concatenated feature set, and to provide the concatenated feature set as input to a second convolutional neural network of the second part 92 of the neural network unit 90. This will in the following be explained in more detail for three reformatted medical images, which had been generated for three different irradiation beam directions (pi, $\varphi_2$, $\varphi_3$, and hence for corresponding three feature sets 30, 31, 32 output by the first part 91 of the neural network unit 90, with reference to FIGS. 8 to 10.

Figure 8:
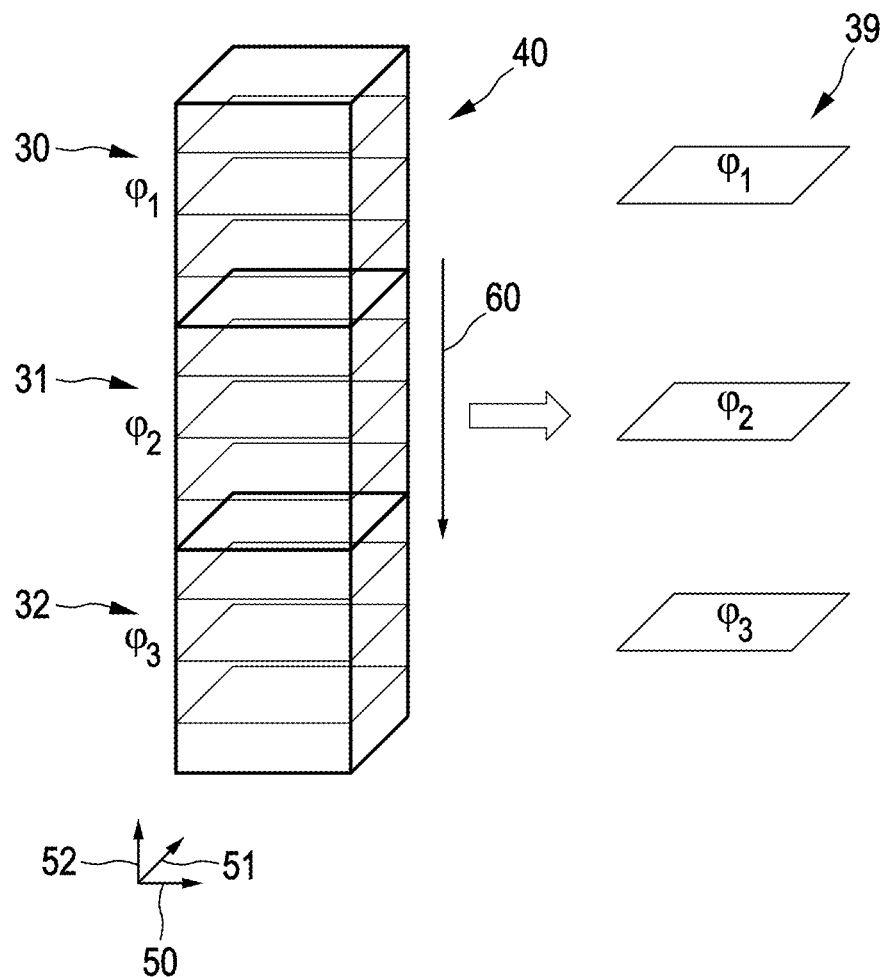
FIG. 8 illustrates schematically and exemplarily a vertical concatenation of feature sets obtained by the first part of the neural network unit for different radiation beam directions.
Figure 9:
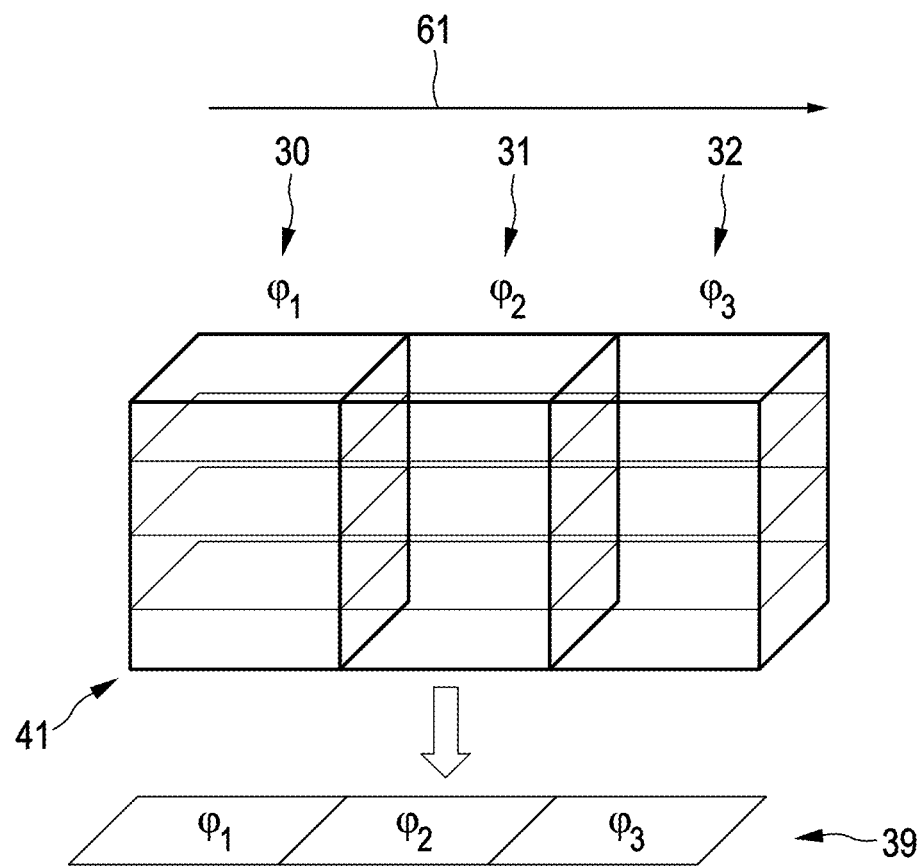
FIG. 9 illustrates schematically and exemplarily a horizontal concatenation of features sets output by the first part of the neural network unit for different radiation beam directions.

The feature sets 30, 31, 32 to be concatenated each comprise a first direction 50 and a second direction 51 corresponding to directions spanning the virtual planar region 13 for which a respective fluence map 93 should be determined and a third direction 52 perpendicular to the first direction 50 and the second direction 51, wherein the concatenation rule defines that the feature sets 30, 31, 32 are concatenated in a concatenation direction 60 being one of the first direction 50, the second direction 51 and the third direction 52. In FIG. 8, the concatenation direction 60 is the third direction 52. This could be regarded as being a vertical concatenation. In FIG. 9, the concatenation direction 61 is the first direction 50. If the concatenation direction is the first direction 50 or the second direction 51, this could be regarded as being a horizontal concatenation. In FIG. 8, the resulting concatenated feature set is indicated by reference sign 40 and in FIG. 9 the resulting concatenated feature set is denoted by reference sign 41.

As can be seen in FIGS. 8 and 9, in these examples the concatenation rules define that the feature sets 30, 31, 32 are concatenated in a concatenation direction 60, 61 such that in this direction the sets of features are grouped with respect to the respective beam direction $\varphi_1$, $\varphi_2$, $\varphi_3$. Thus, in concatenation direction firstly all features of the first beam direction (pi are arranged, secondly all features of the second beam direction $\varphi_2$ are arranged and thirdly all features of the third beam direction $\varphi_3$ are arranged. In FIGS. 8 and 9, the respective planes 39 indicate the final fluence maps which will be determined for the respective beam directions $\varphi_1$, $\varphi_2$, $\varphi_3$.

Figure 10:
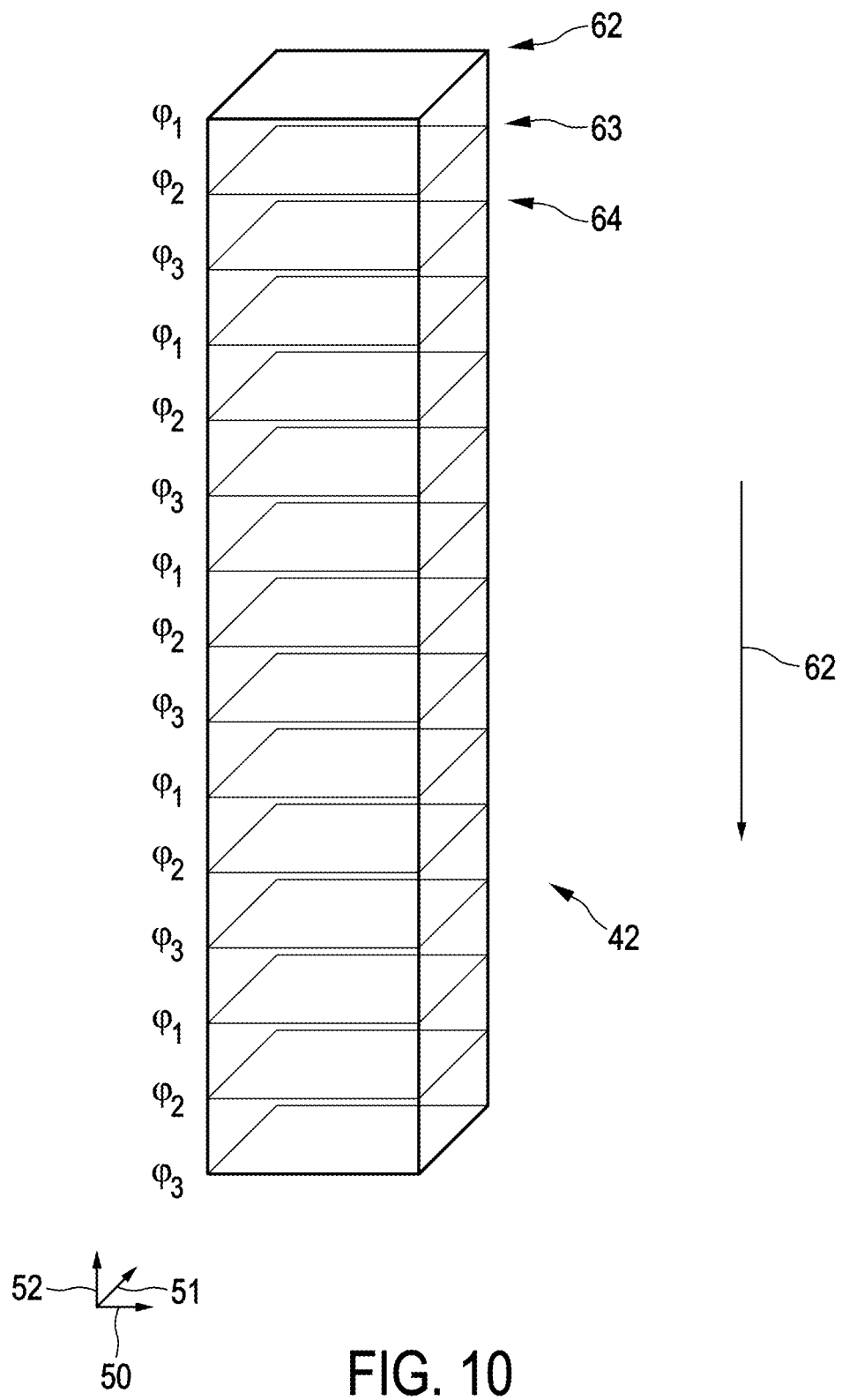
FIG. 10 illustrates schematically and exemplarily a vertical layer-by-layer concatenation of feature sets obtained from the first part of the neural network unit for different radiation beam directions.

However, the concatenation rule can also define that, before concatenating the several feature sets 30, 31, 32, a respective feature set 30, 31, 32 is subdivided into respective feature subsets 62, 63, 64 and that the several feature subsets 62, 63, 64 are concatenated such that feature subsets 62, 63, 64 corresponding to different feature sets 30, 31, 32 and hence to different beam directions $\varphi_1$, $\varphi_2$, $\varphi_3$ are adjacent to each other. Thus, in this case not all features of a first beam direction $\varphi_1$ are followed by all features of a second beam direction $\varphi_2$ further followed by all features of a third beam direction $\varphi$3, but the feature subsets of different beam directions are interleaved as schematically and exemplarily illustrated in FIG. 10. This might be regarded as being a layer-by-layer concatenation, wherein in FIG. 10 a vertical layer-by-layer concatenation is shown. In FIG. 10, the concatenated feature set is indicated by reference sign 42.

The concatenation rule preferentially further defines how the feature sets 30, 31, 32 output by the first part 91 are concatenated depending on the beam directions $\varphi_1$, $\varphi_2$, $\varphi_3$, i.e. depending on the directions of the radiation beams 5 comprising the rays with the ray geometry according to which the respective reformation has been carried out. If it is assumed that $\varphi_1$ is smaller than $\varphi_2$ and that $\varphi_2$ is smaller than $\varphi_3$, in the embodiments described above with reference to FIGS. 8 to 10, the concatenation is carried out in accordance with an increasing or decreasing beam direction, i.e. an increasing or decreasing corresponding angular position. However, the features received from the first part 91 of the neural network unit 90 can also be sorted in another way. For instance, the concatenation can be carried out such that sets of features, which correspond to opposing beam directions, are adjacent to each other in the respective concatenated set of features.

Also the second convolutional network can be a multi-resolution convolutional network. In particular, it can be multi-resolution fully convolutional neural network.

In an embodiment, the second part 92 of the neural network unit 90 is therefore configured to, for a respective feature set 30, 31, 32 to be input into the second convolutional network, determine several second intermediate feature sets having different resolutions by modifying the resolution of the respective feature set and to provide the second intermediate feature sets as input to the second convolutional network such that for a respective second intermediate feature set a respective third intermediate feature set is output, thereby producing several third intermediate feature sets having different resolutions. The several third intermediate feature sets having different resolutions can then be combined such that a second combined feature set is obtained for a respective feature set, which is the output of the neural network unit 90. This combining can include, starting from a third intermediate feature set having the smallest resolution, a) modifying the third intermediate feature set such that its resolution is similar to the next larger one of the resolutions of the several third intermediate feature sets, b) concatenating the modified third intermediate feature set having the modified resolution with the third intermediate feature set having the same resolution, thereby generating a combined feature set, c) modifying the combined feature set such that its resolution is similar to the next larger one of the resolutions of the several third intermediate feature sets, and d) concatenating the modified combined feature set having the modified resolution with the third intermediate feature set having the same resolution, thereby generating a third combined feature set, wherein steps c) and d) are repeated, until a final combined feature set is obtained, which is the output of the neural network unit 90. In this embodiment, the output for a respective beam direction is a respective fluence map. Thus, for a respective beam direction several fluence maps with different resolutions can be generated and these several fluence maps can be combined to the final fluence map for the respective beam direction.

The second convolutional network comprises a network parameter that depends on the concatenation rule. In this embodiment, the network parameters include the size of the filters used by the convolutional layers of the second convolutional network and the stride, wherein the size of the filters and the stride depend on the concatenation direction 60, 61, 62. In particular, the size of the filters and the stride can be determined such that along the concatenation direction 60, 61, 62 the filter acts only on features of a same beam direction or several, but not all, beam directions at a same time. Thus, the size of the filter and the stride can be adapted to the geometry of the reformatted and concatenated image geometry, which can improve the learning of meaningful patterns by the filters.

Figure 11:
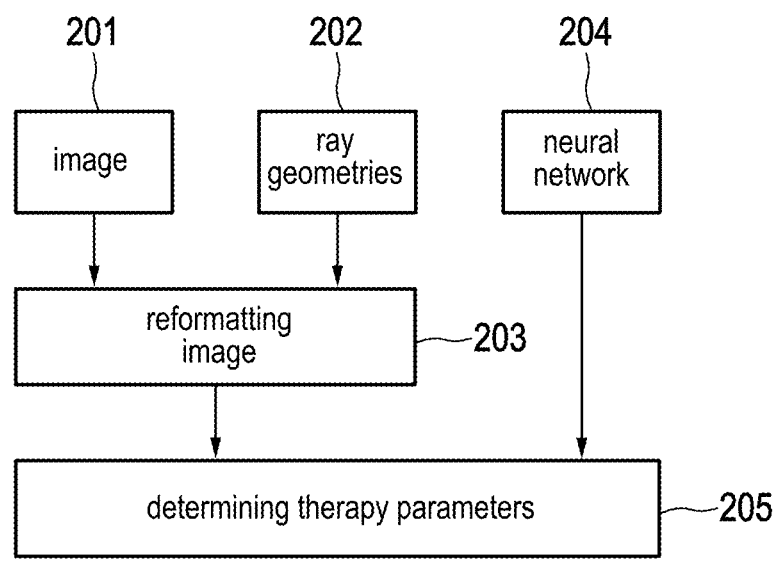
FIG. 11 shows a flowchart exemplarily illustrating an embodiment of a planning method for planning a radiation therapy.

In the following, an embodiment of a planning method for planning a radiation therapy will exemplarily be described with reference to a flowchart shown in FIG. 11.

In step 201, a medical image of a subject is provided by the medical image provider 2, wherein in the medical image a target to be treated with radiation beams is indicated. Also one or several risk structures might be indicated in the medical image. The target and the optional one or several risk structures might be indicated by defining which image elements of the medical image show the target and which image elements of the medical image show the one or several risk structures.

In step 202, ray geometries for different radiation beams to be used for irradiating the target are provided by the ray geometry provider 6, wherein a respective radiation beam comprises respective rays and a respective ray geometry defines, for the respective radiation beam, positions of the respective rays of the respective radiation beam. In particular, for a respective radiation beam a virtual planar region 13 can be defined as described above with reference to FIG. 2, wherein this virtual planar region 13 can be subdivided into bixels and the ray geometry can define that the rays of the radiation beam traverse the bixels, particularly centrally traverse the bixels.

In step 203, the provided medical image is reformatted based on the provided ray geometries by the reformatter 7, resulting in several reformatted medical images, wherein a respective reformatted medical image results from reformatting the provided medical image in accordance with a respective ray geometry. In other words, for each provided ray geometry a respective reformatted medical image can be generated.

In step 204, a neural network unit is provided by the neural network provider 10, wherein the neural network unit has been trained to output radiation therapy parameters being indicative of intensities of rays of radiation beams to be used during the radiation therapy based on an input which depends on reformatted medical images in which a target to be treated with radiation beams is indicated and which have been reformatted in accordance with ray geometries of the rays of the radiation beams. In step 205, the radiation therapy parameters determiner 11 determines the radiation therapy parameters based on the reformatted medical images by using the provided neural network unit, wherein the radiation therapy parameters are indicative of intensities of the rays of the radiation beams to be used for irradiating the target. In particular, the radiation therapy parameters define fluence maps.

Figure 12:
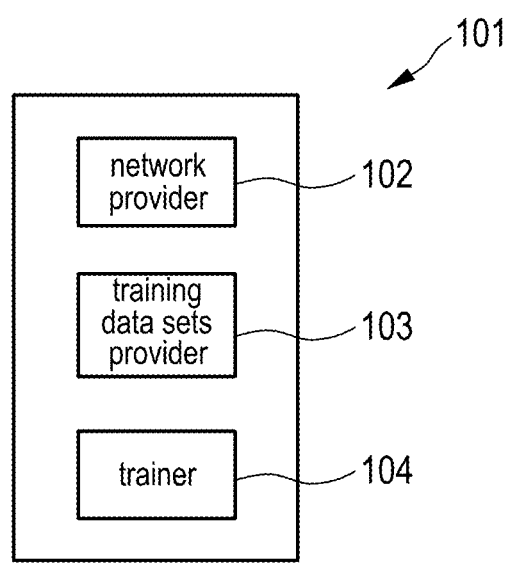
FIG. 12 shows schematically and exemplarily an embodiment of a training apparatus for training a neural network unit.

FIG. 12 shows schematically and exemplarily an embodiment of a training apparatus for training a neural network unit 90. The training apparatus 101 comprises a neural network provider 102 configured to provide a neural network unit to be trained. This neural network unit can be a neural network unit which has not been trained at all up to now, but it can also be a neural network unit which has been trained already and which should be trained further. The provided neural network unit is preferentially of the type described above with reference to FIG. 5, i.e., for instance, it comprises a first part with a first convolutional neural network and a second part with a second convolutional neural network.

The training apparatus 101 further comprises a training data sets provider 103 configured to provide training data sets for training the provided neural network unit. A training data set comprises, as input training data, a) a reformatted medical image, which is a medical image of the subject, in which the target to be treated with radiation beams and optionally a risk structure are indicated and which has been reformatted in accordance with a ray geometry of a radiation beam to be used for irradiating the target, wherein the radiation beam comprises rays and the ray geometry defines positions of the rays of the radiation beam, and, as output training data, b) radiation therapy parameters like fluence maps being indicative of intensities of the rays of the radiation beams to be used for irradiating the target.

The training apparatus 101 further comprises a trainer 104 configured to modify the provided neural network such that a deviation measure being indicative of a deviation between a) obtained output data, which are obtained if the input training data of the training data sets are input into the neural network unit, and b) the output training data of the training data sets is reduced.

In an embodiment, the training data sets provider 103 is configured to also provide, for a training data set, a training dose distribution across the target and the optional risk structure, if present, wherein the trainer 104 is configured to determine a dose distribution across the target and the optional risk structure, if present, which would be obtained if a radiation therapy in accordance with the obtained output data were carried out and wherein the deviation measure is also indicative of a deviation between a) the determined dose distribution and b) the training dose distribution. For determining the dose distribution across the target and the optional risk structure, which would be obtained if a radiation therapy in accordance with the obtained output data were carried out, the trainer 104 can be configured to carry out a corresponding simulation, wherein the radiation therapy is simulated based on the obtained radiation therapy parameters and the corresponding input training data. However, also known functional relations can be used for determining the dose distribution across the target and the optional risk structure, which would be obtained if a radiation therapy in accordance with the obtained output data were carried out.

Figure 13:
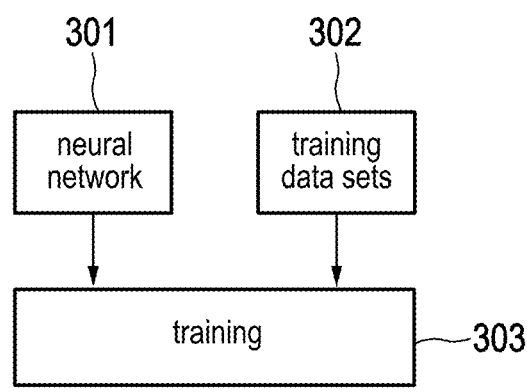
FIG. 13 shows a flowchart exemplarily illustrating an embodiment of a training method for training a neural network unit.

In the following, an embodiment of a training method for training a neural network unit will exemplarily be described with reference to a flowchart shown in FIG. 13.

In step 301, a neural network unit, which should be trained, is provided by the neural network provider 102. In step 302, training data sets for training the provided neural network unit are provided by the training data sets provider 103, wherein a training data set comprises, as input training data, a) a reformatted medical image, which is a medical image of a subject, in which a target to be treated with radiation beams is indicated and which has been reformatted in accordance with a ray geometry of a radiation beam to be used for irradiating the target, wherein the radiation beam comprises rays and the ray geometry defines positions of the rays of the radiation beams, and, as output training data, b) radiation therapy parameters being indicative of intensities of the rays of the radiation beam to be used for irradiating the target. In step 303, the trainer 104 modifies the provided neural network unit such that a deviation measure being indicative of a deviation between a) obtained output data, which are obtained if the input training data of the training data sets are input to the neural network unit, and b) the output training data of the training data sets is reduced.

Radiation therapy is generally used as a curative treatment for cancer and can also be used as an adjuvant, neo-adjuvant and palliative cancer treatment. If the neural network unit were not used, it would be required to balance sets of radiation delivery objectives for target coverage with constraints to spare risk structures for each patient, taking into account patient specific locations, shapes and sizes of the one or several targets, the patient specific anatomy, et cetera, in order to achieve a safe and effective treatment plan. Such a radiation therapy planning (RTP) process, which does not use the neural network unit as described in the present patent application, in order to compute radiation delivery segments that can produce a prescribed dose, is very labor intense and iterative, requiring highly specialized personnel whose skills and experience also affects the planning quality. The radiation therapy planning apparatus 1 described above with reference to, for instance, FIG. 3 overcomes these disadvantages. In particular, the planning apparatus 1 allows to directly estimate fluence maps or even segment openings, i.e., leaf openings of a multileaf collimator, which could be directly used for carrying out a radiation therapy or which could be used as a starting point for a subsequent plan optimization.

In order to carry out a subsequent plan optimization, the radiation therapy parameters determiner can be adapted to apply a plan optimization algorithm for optimizing the determined radiation therapy parameters which have been determined by using the neural network unit. This can lead to a further improved quality of the finally determined radiation therapy parameters, wherein these further improved radiation therapy parameters can still be obtained relatively fast, because the optimization algorithm has a very good starting point, i.e. the radiation therapy parameters which have been determined already by using the neural network unit. The optimization algorithm can be a known optimization algorithm which is generally used for optimizing radiation therapy parameters. For instance, the optimization algorithms disclosed in the patent applications WO 2019/185499 A1 and WO 2016/046683 A2 or in the article "Utilizing Problem Structure in Optimization of Radiation Therapy" by Fredrik Carlsson, Doctoral dissertation, Kungl Tekniska Hogskolan, Stockholm, 2008, which are herewith incorporated by reference, can be used.

During the training, the neural network unit 30 automatically learns to generate high-quality radiotherapy plans, i.e. high-quality radiation therapy parameters, by deciphering patterns in features from the initial medical image and contours of the target and optional risk structures indicated in the medical image and by relating them directly to, for instance, fluence maps or, for instance, leaf openings of the multileaf collimator.

The planning apparatus 1 is configured to reformat the provided medial image, which is preferentially a three-dimensional image like a CT volume, and masks of the target and the optional risk structures, i.e. the indications of the target and the optional risk structures in the medical image, according to a delivery protocol and a geometry of rays associated with each bixel in a fluence plane 13. The delivery protocol at least defines the positions of the radiation source relative to the subject and hence, together with the definition that the rays traverse the bixels in the fluence plane, the position and orientation of each ray to be used for the reformatting.

The reformatted medical images are then used in the neural network unit which has the above described architecture tailored to estimate fluence maps or, for instance, leaf openings and radiation intensity per leaf opening. The training data sets used for training the neural network unit can include previous plans with leaf openings, radiation intensity per leaf opening and optionally also a planned dose distribution. It is especially preferred that during training the leaf openings and the radiation intensities per leaf opening are reproduced, wherein as an additional training objective the respective planned radiation dose distribution may be compared with a radiation dose distribution computed on the basis of the leaf openings and the radiation intensity per leaf opening predicted by the neural network unit.

Figure 2:
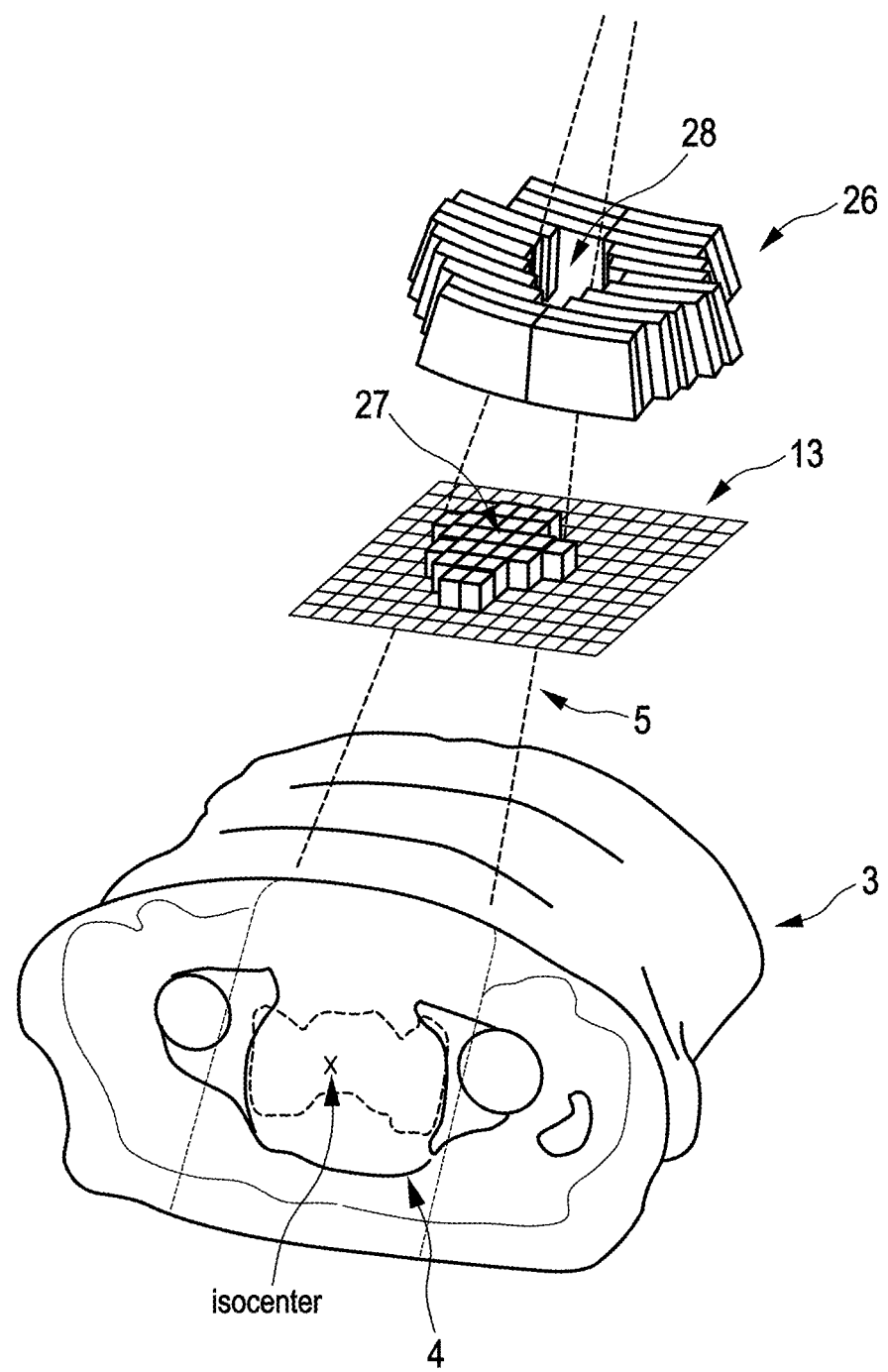
FIG. 2 illustrates schematically and exemplarily a fluence plane between a subject and a multileaf collimator.

As can be seen in FIG. 2, the virtual planar region 13, i.e. the fluence plane 13, is subdivided into bixels, wherein in FIG. 2 each bixel comprises a fluence for a single ray and the entire respective fluence map including all bixels describe the fluence for a single beam direction, wherein a respective beam 5 includes rays traversing the bixels. The subdivision of the fluence map 13 can be regarded as being a subdivision in bixel rows and bixel columns. The number of the bixels for a single beam direction is hence the number of bixels rows multiplied by the number of bixel columns. The reformatter is preferentially adapted to reformat the provided medial image together with the masks of the target and the optional risk structure according to the geometry of the rays passing through the bixel centers. In that way, for a respective single beam direction, a reformatted medical image, i.e. a reformatted volume, is determined having a dimension, i.e. a number of elements, being defined by the number of bixel rows multiplied by the number of bixel columns multiplied by the length of the profile, wherein each element of the respective volume comprises a vector with at least one image display value like an image intensity and a mask value. In an embodiment, such a volume, being a reformatted medical image, can be defined for each beam direction and for each desired leaf opening which should be determined for a respective beam direction, wherein the number of desired leaf openings and the number of beam directions define the number of volumes of this kind. If, for instance, the radiation therapy should be carried out in accordance with a step-and-shoot protocol, wherein for a same beam direction several leaf openings and hence several beams are used, the number of volumes to be input into the neural network unit is preferentially identical to the number of beam directions multiplied by the number of desired leaf openings which should be used per beam direction, if for each beam direction the same number of leaf openings should be used. For instance, if 9 beam directions and for each beam direction 10 desired leaf openings are used, 90 input volumes can be determined by reformatting the provided initial medial image indicating the target and optionally also one or several risk structures in accordance with corresponding 90 different ray geometries. In case of a volumetric modulated arc therapy (VMAT) protocol, discrete directions are used, wherein, for instance, a 360° arc might be used with an angular resolution of 4° degree leading to 90 volumes to be input into the neural network unit.

In an embodiment, the target covers a so-called treatment center, wherein in an embodiment the treatment center coincides with an isocenter of the radiation therapy system.

Preferentially, the parameters defining the number of input volumes and the number of elements of the input volumes are chosen such that, for different treatments to be planned, the number of input volumes and the number of image elements of the input volumes is the same, because this can simplify the inputting of the volumes into the neural network unit.

For determining the radiation therapy parameters, i.e., for instance, the fluence maps or the leaf openings and intensities of the radiation provided by the radiation source per leaf opening, from the reformatted volumes, i.e. from the reformatted medical images, a neural network unit is proposed having a network architecture composed of two parts.

The first part reduces each of the, for instance, N reformatted volumes, i.e. N reformatted medical images, from its original dimension via a series of convolutions to a smaller dimension. Each reformatted volume has an original dimension defined by the number of bixel rows multiplied by the number of bixel columns multiplied by the length of the profile, i.e. the number of elements of the reformatted volume perpendicular to the bixel plane, multiplied by the number of values assigned to a respective image element. For instance, if to an image element a) an image display value, b) a task mask value and c) a risk structure mask value are assigned, the number of values assigned to a respective image element is three. However, also more or less values can be assigned to a respective image element. The task mask value can be a binary value, i.e. just indicating whether the respective image element shows a target or not, or it can be a value being indicative for a dose related value like a desired target dose. The risk structure value can be a binary value, i.e. just indicating whether the respective image element shows a risk structure or not, or it can be a value being indicative for a dose related value like a maximum dose.

The length of the profile can be defined, for instance, by the intersection of the rays with the borders of the original medical image or with the borders of the subject shown in the original medical image. Generally, a region of interest might be determined automatically or manually and the length of the profile might be defined by an intersection of the region of interest with the respective ray. The region of interest can be the entire image, but is can also be a smaller region like the borders of the subject or the borders of the target.

The dimension of the output of the first part for a respective single reformatted volume is defined by the number of bixel rows multiplied by the number of bixel columns multiplied by the number of filters of the last layer of the first convolutional neural network of the first part. The number of filters of the last layer of the first convolutional neural network of the first part is preferentially chosen to be much smaller than the length of the original profile. This is motivated by the idea that information along the rays can be integrated/summed up or condensed.

The resulting N feature volumes, i.e. the resulting N feature sets output by the first part of the neural network unit, are combined and fed into the second part of the neural network unit. This second part has the task to incorporate the effects of the other radiation beams onto a profile irradiated by one single radiation beam, i.e. onto the values along the respective one radiation beam. For instance, if two neighboring and hence overlapping radiation beams are considered, the effect of the second radiation beam onto the profile irradiated by the first radiation beam has to be taken into account, when the radiation therapy parameters, i.e., for instance, the fluence map, for the first radiation beam is determined.

The first convolutional neural network is preferentially a multi-resolution three-dimensional convolutional neural network. It can be, for instance, the F-net disclosed in the article "Foveal fully convolutional nets for multi-organ segmentation" by T. Brosch and A. Saalbach, Medical Imaging 2018: Image Processing, volume 10574, p. 105740U, International Society for Optics and Photonics (2018), which is herewith incorporated by reference. Preferentially, as input for the first convolutional network, a reformatted volume, i.e. a reformatted medical image, corresponding to one radiation beam and several downsampled volumes is used, i.e. volumes are used, which contain the same anatomical content, but in different resolutions, as described above with reference to FIG. 6. For example, an original reformatted volume, i.e. an original reformatted medical image to be input into the first convolutional neural network, might have a dimension of 40×40×200 and the lower resolution volumes might have dimensions of 20×20× 100 and 10×10×50, only considering one value per image element for ease of explanation and for allowing to show the different resolutions as different boxes in the figures. For each of these three volumes having different resolutions, the first convolutional neural network applies a series of convolutions preferentially followed by batch normalization and an activation function such as ReLU. This process can be denoted by "CBR" and is indicated in the right part of FIG. 6. If these operations are followed by an upsampling procedure, this is indicated by the abbreviation "CBRU" as can be seen, for instance, in FIG. 7. The application of the first convolutional neural network results, for each resolution level, in a respective output volume with the same width and depth as the respective input volume, but with a reduced length. For example, the above described three volumes having the different resolutions as input into the first convolutional neural network can lead to three output volumes having the dimensions 40×40×5, 20×20×5 and 10×10×5. The output volumes, i.e. the output feature sets, which have the different resolutions, are respectively upsampled and concatenated with the respective next higher resolution output volume as described above with reference to FIG. 7. This upsampling and concatenation can be carried out in accordance with the content of the above mentioned article by T. Brosch and A. Saalbach.

Although in the above described example the length, i.e. the third dimension perpendicular to the fluence plane dimensions, is the same for each output volume, i.e. in the provided example it is "5" for each resolution, this is not necessarily required for all resolutions, because, before concatenating a lower resolution volume with another output volume having the next higher resolution, one of these volumes or both volumes could be resampled such that they have the same dimension in the length direction, before concatenating them.

After the output feature volumes having different resolutions have been upsampled and concatenated, the resulting feature set has a width and depth which is identical to the width and depth of the original reformatted volume such that the width and depth preferentially correspond to the number of bixels of the fluence plane, i.e. of the virtual planar region 13, for which the fluence map should be determined. Thus, the width and the depth of the resulting feature set has the size of the fluence map to be determined for the respective radiation direction. In the above example, the width and depth of the feature set output by the first convolutional neural network for a respective reformatted medical image is hence 40 and 40 such that fluences will be determined for 40×40 bixels.

The first part of the neural network unit 30 is preferentially applied to all N reformatted volumes, i.e. to all N reformatted medical images, wherein a respective reformatted volume corresponds to a respective beam direction for which radiation therapy parameters like a fluence map or directly a leaf opening or a radiation intensity should be determined. The network weights of the first convolutional neural network are preferentially shared due to the radial symmetry of the setup/problem. In particular, each profile, i.e. each set of values along a respective ray, is treated equally by the neural network, i.e. the same convolutional filters are applied to all single profiles, because it is reasonable to assume that the features the convolutional filters are "looking for" should be the same in all profiles, i.e. should not depend on the respective angle.

After the N feature volumes, i.e. the resulting N feature sets, have been output by the first part of the neural network unit, these N feature volumes are combined by concatenating them. In particular, they can be concatenated as described above with reference to FIGS. 8 to 10. The ordering of the N feature volumes before concatenation can be chosen to reflect the symmetry of the setup, i.e. it can be chosen depending on the directions of the radiation beams. For example, if the directions of the radiation beams are defined by the beam angles 0°, 10°, . . . , 180°, 190°, . . . , 350°, the ordering before concatenation may be chosen to be 0°, 180°, 10°, 190°, . . . , in order to reflect the fact that counter-propagating beam pairs, i.e., for instance, having beam angles of 0° and 180°, have a strong influence on the respective fluence maps.

The resulting three-dimensional concatenated volume is fed into the second convolutional neural network which is preferentially a fully convolutional neural network, preferentially in a multi-resolution approach as described above. The output of the second convolutional neural network has a dimension being defined by the number of bixel rows multiplied by number of bixel columns multiplied by number of beam directions or number of beam angles such that for each beam direction or beam angle a respective two-dimensional fluence map is determined in this embodiment. Parameters of the second convolutional neural network are preferentially selected in dependence of the way the feature volumes have been concatenated before being input into the second convolutional neural network. For example, the kernel size, i.e. the size of the filter, and the stride may be chosen such that along the respective concatenation direction the convolutional kernel, i.e. the convolutional filter, either acts only within one angle subvolume, i.e. a single feature volume or feature set that has been determined for a single beam angle or beam direction, or on a number M of complete subvolumes, wherein M is equal to or smaller than N. For instance, in the case of vertical concatenation as described above with reference to FIG. 8 and three layers per subvolume, a kernel size of 3 and a stride of 3 or a kernel size of 6 or 9 or 12 or 15 etc. and a stride of 3 might be chosen. Alternatively, the N subvolumes can be viewed as N input channels such that each convolutional kernel of size, for instance, 3×3×3 has 3×3×3×N weights such that in the first convolutional layer of the second convolutional neural network the convolutions do not stride across the boundaries between the different beam angles.

The neural network unit 30 is preferentially trained end-to-end. Thus, in an embodiment anatomical input volumes being anatomical input medical images like CT images, wherein in the anatomical input volumes one or several risk structures and targets can be indicated, serve as training inputs and fluence maps and optionally also target doses can serve as training targets. During the training, the loss function, i.e. the deviation measure, can be, for instance, a voxel-wise loss between the reference fluence maps, i.e. the training fluence maps provided as training targets, and the fluence maps determined by the neural network unit to be trained. The loss function can be, for instance, an L1 loss function or an L2 loss function. The deviation measure can hence be based on a summation of absolute differences of fluence values of corresponding bixels (L1), or the deviation measure can be based on a summation of squared differences between fluence values of corresponding bixels (L2), of a respective training fluence map and a respective fluence map output by the neural network unit to be trained. Of course, also other deviation measures being indicative of deviations between the training fluence maps and the fluence maps output by the neural network unit to be trained can be used.

In addition to considering deviations between the fluence maps, also deviations between three-dimensional dose distributions can be used for the training Thus, a three-dimensional dose distribution can be incorporated in the deviation measure, particularly in the loss function. For determining the three-dimensional dose distribution based on fluence maps provided for different beam directions, known algorithms can be used. For instance, a known dose influence matrix P can be used, which yields the three-dimensional dose distribution if multiplied with the fluence maps b determined for the different beam directions. For instance, the dose influence matrix P can be provided as described in the above mentioned Doctoral dissertation by Fredrik Carlsson, which is herewith incorporated by reference.

Since each fluence map is two-dimensional, the several fluence maps b are three-dimensional, i.e. b is three-dimensional and hence can be regarded as being a matrix b. The output of the matrix multiplication P.b, i.e. the three-dimensional dose distribution, can also be regarded as being a matrix which can be named d. Thus, based on the training fluence maps and the dose influence matrix P, training dose distributions d can be calculated. Correspondingly, based on the dose influence matrix P and fluence maps b' determined by using the neural network unit to be trained, obtained or predicted three-dimensional dose distributions d' can be determined. A deviation measure can also consider deviations between the three-dimensional dose distributions d and d' during the training. Also this deviation measure can be based on an L1 loss or an L2 loss, wherein also another deviation measure being indicative of a deviation between d and d' can be used during the training. In an embodiment, the total training loss to be used during the training can be a combination of the fluence map loss and the dose loss with a tunable relative weight between these two losses. Thus, the total training loss might be defined by the fluence map loss plus the dose loss multiplied by a weight. By incorporating the dose loss, errors on more relevant bixels are penalized stronger than errors on less relevant bixels.

Data augmentation techniques may be used, but in a modified way. For instance, a CT planning image together with masks of target and risk organs may be deformed and planning techniques may be used to generate additional data sets.

For inference, the planning image and the mask of the target and the optional one or several risk structures, i.e. the initial medical image, is reformatted according to a desired protocol. Different kinds of protocols corresponding to different reformatting may be used with a same neural network unit as long as the number N of initial reformatted medical images and the number of bixels is constant, because this allows for a very simple mapping to the network structure. Inference may be combined with known techniques to improve the result such as ensembling, for instance, network results generated with different parameters may be combined. In particular, a number of networks might be used and the result of the various networks might be averaged.

Although in above described embodiments the training apparatus and the planning apparatus are two separate devices, the planning apparatus and the training apparatus can also be integrated. In particular, the neural network provider of the planning apparatus can also be or include the training apparatus such that the neural network provider is also able to train an initial or an already trained neural network unit.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the provision of the medial image, the provision of the ray geometries, the reformatting of the provided medical image, the provision of the neural network unit, the determination of the radiation therapy parameters, et cetera, performed by one or several units or devices, can be performed by any other number of units or devices. For example, above described steps 201 to 205 or 301 to 303 can be performed by a single unit or by any other number of different units. These procedures and/or the control of the planning apparatus in accordance with the planning method and/or the control of the training apparatus in accordance with the training method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a planning apparatus for planning a radiation therapy. A medical image, in which a target to be irradiated is indicated, is reformatted based on ray geometries to be used during the radiation therapy to be planned, resulting in several reformatted medical images. Radiation therapy parameters being indicative of intensities of rays to be used for irradiating a target are determined based on the reformatted medical images by using a neural network unit. This allows to determine high quality radiation therapy parameters and hence allows for an improved planning of a radiation therapy. In particular, radiation and absorptions physics can be captured better, which can lead to the improved quality.

The invention claimed is:

1. A planning apparatus for planning a radiation therapy, wherein the planning apparatus comprises:
   a medical image provider configured to provide a medical image of a subject, wherein in the medical image (3) a target to be treated with radiation beams is indicated,
   a ray geometry provider configured to provide ray geometries for different radiation beams to be used for irradiating the target, wherein a respective radiation beam comprises respective rays and a respective ray geometry defines, for the respective radiation beam, positions of the respective rays of the respective radiation beam,
   a reformatter configured to reformat the provided medical image based on the provided ray geometries, resulting in several reformatted medical images, wherein a respective reformatted medical image results from reformatting the provided medical image in accordance with a respective ray geometry,
   a neural network provider configured to provide a neural network unit which has been trained to output radiation therapy parameters being indicative of intensities of rays of radiation beams to be used during the radiation therapy based on an input which depends on reformatted medical images in which a target to be treated with radiation beams is indicated and which have been reformatted in accordance with ray geometries of the rays of the radiation beams,
a radiation therapy parameters determiner configured to determine radiation therapy parameters being indicative of intensities of the rays of the radiation beams to be used for irradiating the target based on the reformatted medical images by using the provided neural network unit.

2. The planning apparatus as defined by claim 1, wherein the neural network unit comprises a first part with a first convolutional network and a second part with a second convolutional network, wherein the first part receives the reformatted medical images as input and provides its output to the second part, wherein the second part receives the output of the first part and outputs the radiation therapy parameters, wherein the first convolutional network comprises a sequence of convolutional layers, wherein each convolutional layer comprises one or several filters, wherein the first convolutional layer of this sequence receives the reformatted medical images (8, 9).

3. The planning apparatus as defined by claim 2, wherein the number of the filters of the last convolutional layer of the sequence is smaller than the number of elements of a respective reformatted medical image in a direction of a respective ray.

4. The planning apparatus as defined by claim 2, wherein the first part is configured to, for a respective reformatted medical image,
determine several intermediate reformatted medical images having different resolutions by modifying the resolution of the respective reformatted medical image,
provide the intermediate reformatted medical images as input to the first convolutional network such that for a respective intermediate reformatted medical image a respective first intermediate feature set is output by the first convolutional network, thereby producing several first intermediate feature sets having different resolutions,
combine the several first intermediate feature sets having different resolutions such that a feature set is obtained for a respective reformatted medical image, which is to be input into the second part of the neural network, wherein the combining includes, starting from a first intermediate feature set having the smallest resolution, a) modifying the first intermediate feature set such that its resolution is similar to the next larger one of the resolutions of the several first intermediate feature sets, b) concatenating the modified first intermediate feature set having the modified resolution with the first intermediate feature set having the same resolution, thereby generating a combined feature set, c) modifying the combined feature set such that its resolution is similar to the next larger one of the resolutions of the several first intermediate feature sets, and d) concatenating the modified combined feature set having the modified resolution with the first intermediate feature set having the same resolution, thereby generating a further combined feature set, wherein steps c) and d) are repeated, until a final combined feature set is obtained, which is the feature set to be input into the second part of the neural network unit.

5. The planning apparatus as defined by claim 2, wherein the first part of the neural network unit is configured to output for a respective reformatted medical image a respective feature set, wherein the second part of the neural network unit is configured to concatenate the feature sets output by the first part in accordance with a concatenation rule in a concatenation direction, thereby generating a concatenated feature set and to provide the concatenated feature set as input to the second convolutional network.

6. The planning apparatus as defined by claim 5, wherein the ray geometry provider is configured to define for a respective radiation beam a respective virtual planar region between a radiation source configured to generate the radiation beams and the subject, wherein the respective virtual planar region is subdivided into bixels and wherein a respective ray geometry defines that a respective ray traverses a respective bixel, wherein the feature sets to be concatenated each comprise a first direction and a second direction corresponding to directions spanning the virtual planar region and a third direction perpendicular to the first direction and the second direction, wherein the concatenation rule defines that the concatenation direction is one of the first direction, the second direction and the third direction.

7. The planning apparatus as defined by claim 2, wherein the second convolutional network comprises a network parameter that depends on the concatenation rule.

8. The planning apparatus as defined by claim 7, wherein the second convolutional neural network comprises a size of a filter and a stride as network parameters, wherein the size of the filter and the stride are determined such that along the concatenation direction the filter acts only on features of a same beam direction or several, but not all, beam directions at a same time.

9. A radiation therapy system comprising:
a radiation source configured to generate radiation to be directed to a target of a subject to be treated,
a multileaf collimator configured to collimate the generated radiation with different leaf openings, in order form different radiation beams,
a mover configured to move the radiation source and the multileaf collimator relative to the subject such that the target is irradiatable by the different radiation beams in different irradiation directions,
a planning apparatus for planning a radiation therapy as defined by claim 1, wherein the planning apparatus is configured to determine radiation therapy parameters being indicative of intensities of rays of the radiation beams to be used for irradiating the target,
a controller configured to control the radiation source, the multileaf collimator and the mover depending on the determined radiation therapy parameters.

10. A training apparatus for training a neural network unit, wherein the training apparatus comprises:
a neural network provider configured provide a neural network unit to be trained,
a training data sets provider configured to provide training data sets for training the provided neural network unit, wherein a training data set comprises as input training data a) a reformatted medical image, which is a medical image of a subject, in which a target to be treated with radiation beams is indicated and which has been reformatted in accordance with a ray geometry of a radiation beam to be used for irradiating the target, wherein the radiation beam comprises rays and the ray geometry defines positions of the rays of the radiation beam, and as output training data b) radiation therapy parameters being indicative of intensities of the rays of the radiation beam to be used for irradiating the target, a trainer (104) configured to modify the provided neural network unit such that a deviation measure being indicative of a deviation between a) obtained output data, which are obtained if the input training data of the training data sets are input into the neural network unit, and b) the output training data of the training data sets is reduced.

11. The training apparatus as defined by claim 10, wherein the training data sets provider is configured to also provide, for a training data set, a training dose distribution across the target, wherein the trainer is configured to determine a dose distribution across the target, which would be obtained if a radiation therapy in accordance with the obtained output data were carried out, and wherein the deviation measure is also indicative of a deviation between a) the determined dose distribution and b) the training dose distribution.

12. A planning method for planning a radiation therapy, wherein the planning method comprises:
providing a medical image of a subject by a medical image provider, wherein in the medical image a target to be treated with radiation beams is indicated,
providing ray geometries for different radiation beams to be used for irradiating the target by a ray geometry provider, wherein a respective radiation beam comprises respective rays and a respective ray geometry defines, for the respective radiation beam, positions of the respective rays of the respective radiation beam,
reformatting the provided medical image based on the provided ray geometries by a reformatter, resulting in several reformatted medical images, wherein a respective reformatted medical image results from reformatting the provided medical image in accordance with a respective ray geometry,
providing a neural network unit by a neural network provider, wherein the neural network unit has been trained to output radiation therapy parameters being indicative of intensities of rays of radiation beams to be used during the radiation therapy based on an input which depends on reformatted medical images in which a target to be treated with radiation beams is indicated and which have been reformatted in accordance with ray geometries of the rays of the radiation beams,
determining radiation therapy parameters by a radiation therapy parameters determiner based on the reformatted medical images by using the provided neural network unit, wherein the radiation therapy parameters are indicative of intensities of the rays of the radiation beams to be used for irradiating the target.

13. A planning computer program for planning a radiation therapy, the computer program comprising program code means for causing a planning apparatus to carry out the steps of the planning method as defined by claim 12, when the computer program is run on a computer controlling the planning apparatus.

14. A training method for training a neural network unit, wherein the training method comprises:
providing a neural network unit, which should be trained, by a neural network provider,
providing training data sets for training the provided neural network unit by a training data sets provider, wherein a training data set comprises as input training data a) a reformatted medical image, which is a medical image of a subject, in which a target to be treated with radiation beams is indicated and which has been reformatted in accordance with a ray geometry of a radiation beam to be used for irradiating the target, wherein the radiation beam comprises rays and the ray geometry defines positions of the rays of the radiation beam, and as output training data b) radiation therapy parameters being indicative of intensities of the rays of the radiation beam to be used for irradiating the target,
modifying the provided neural network unit such that a deviation measure being indicative of a deviation between a) obtained output data, which are obtained if the input training data of the training data sets are input into the neural network unit, and b) the output training data of the training data sets is reduced, by a trainer.

15. A training computer program for training a neural network unit, the computer program comprising program code means for causing a training apparatus to carry out the steps of the training method as defined by claim 14, when the computer program is run on a computer controlling the training apparatus.

* * * * *